United States Patent [19]

Mason et al.

[11] 4,393,717

[45] Jul. 19, 1983

[54] APPARATUS FOR TESTING MEDICINAL TABLETS

[75] Inventors: Donald L. Mason, Washington; Warren A. McAllister, Greenville, both of N.C.

[73] Assignee: Burroughs Wellcome Co., Research Triangle Park, N.C.

[21] Appl. No.: 222,825

[22] Filed: Jan. 6, 1981

[51] Int. Cl.³ ............................................. G01N 3/08
[52] U.S. Cl. .................................... 73/821; 33/174 L; 209/558; 209/599
[58] Field of Search ............ 33/147 E, 147 N, 143 L, 33/174 L, 178 E; 73/78, 821, 825; 209/558, 599, 601, 604

[56] References Cited

U.S. PATENT DOCUMENTS

| | | | |
|---|---|---|---|
| 2,643,936 | 7/1953 | Albrecht | 73/821 |
| 3,168,196 | 2/1965 | Harder | 33/147 X |
| 3,282,116 | 11/1966 | Jones | 209/604 X |
| 3,417,476 | 12/1968 | Martens | 209/604 X |
| 3,593,427 | 7/1971 | Abarotin | 33/174 X |
| 3,610,034 | 10/1971 | Gunn et al. | 73/821 |
| 3,743,093 | 7/1973 | Klancnik | 209/601 X |
| 3,943,757 | 3/1976 | Wilhelm, Jr. | 73/78 |
| 4,236,413 | 12/1980 | Schmid et al. | 73/821 |

*Primary Examiner*—Herbert Goldstein
*Attorney, Agent, or Firm*—Donald Brown

[57] ABSTRACT

Apparatus for testing medicinal tablets for thickness, diameter and hardness wherein there is a support for receiving and supporting tablets for testing one at a time, a gauge movable relative to the support to measure the thickness, a gauge movable relative to the support to both measure the thickness and breaking strength, a sweeper movable relative to the support to clear the crushed tablets therefrom and control circuitry including a computer for controlling the sequence of operations and recording the values measured.

16 Claims, 8 Drawing Figures

APPARATUS FOR TESTING MEDICINAL TABLETS

BACKGROUND OF INVENTION

Heretofore, such apparatus as has been available for testing medicinal tablets for thickness, diameter and hardness has been limited to the use of gauge plates containing holes for sizing and pressure gauges. Such apparatus is inaccurate and inconclusive, requires manual counting and recording and constitutes a considerable waste of the time of personnel involved. It is the purpose of this invention to automate tablet testing so as to enable automatically testing tablets in a predetermined group of tablets for thickness, diameter and hardness and to record the test readings on the basis of average measurements, the range and any out of limit tablets.

SUMMARY OF INVENTION

As herein illustrated, the invention resides in apparatus for testing medicinal tablets for thickness, diameter and hardness comprising a support for receiving tablets one at a time for testing, means movable relative to the support in a direction perpendicular to the thickness of the tablet to measure the thickness of the tablet, means movable relative to the support at a direction of right angle to the thickness to measure the diameter of the tablet, said latter means being further movable to crush the tablet to thus measure the hardness and means for effecting movement of the aforesaid means in sequence and for repeating said sequence of operations for a predetermined number of tablets. The support comprises a flat, unyielding, horizontal surface and a flat, unyielding, vertical surface and the first means is movable perpendicular with respect to the horizontal support and the second means is movable perpendicularly with respect to the vertical support. The first and second means are, respectively, a thickness gauge and a ram, and the third means comprises power-operable devices for effecting reciprocation of the gauge and ram to, respectively, advance and retract the gauge and advance and retract the ram. There is also means movable relative to the horizontal surface following retraction of the ram to sweep a crushed tablet from the support. The last-named means comprises a scraper provided with right-angularly disposed surfaces which, respectively, have scraping contact with the horizontal and vertical surfaces of the support. The means for effecting reciprocation of the gauge, ram and scraper are double-acting cylinders and piston assemblies. The cylinder and piston assemblies by means of which the gauge and ram are reciprocated are provided with piston rods which extend from the opposite ends of the piston through the opposite ends of the cylinder, the gauge and the ram are fixed to the extremities of the rods extending from one end and there is means at the extremities of the rods at the other end for determining the measurements of thickness and diameter. The aforesaid means comprise sensing means determinative of the movement of the rods and said sensing means comprise diodes mounted to the rods for movement therewith and photopotentiometers supported to be traversed by the diodes. There is a pressure transducer connected to the cylinder containing the ram operable by a change in pressure in the cylinder when a tablet fails, to register the breaking pressure. There is means for delivering tablets from a predetermined group of tablets onto the support one at a time comprising an inclined trough supported at its lower end above the support, a vibrator for vibrating the trough, means for delivering tablets to the upper end of the trough comprising a part containing a hole of such size as to permit the tablets to pass through and a carousel supported for rotation above the part provided with a plurality of tubular containers spaced peripherally thereof having open lower and upper ends, with their lower ends adjacent the part, means for rotating the carousel to successively bring the lower open ends of the containers above the opening in the part and means for controlling movement of the carousel to move successive containers into position above the opening. There is a sensor positioned in the path of movement of a tablet dropping from the lower end of the trough onto the support to disable the vibrator, said sensor being further operable in the event that a second tablet falls from the lower end of the trough onto the support within a predetermined interval following the first to disable the vibrator, initiate operation of the scraper to clear the support of the two tablets and reenable the vibrator. The photopotentiometers, the pressure transducer and the photoelectric sensor are designed to produce signals of a predetermined kind, and there is microcomputer means conditioned to respond to such signals to produce the sequence of operations required and a terminal printer.

The invention will now be described in greater detail with reference to the accompanying drawings, wherein.

Figure 7:
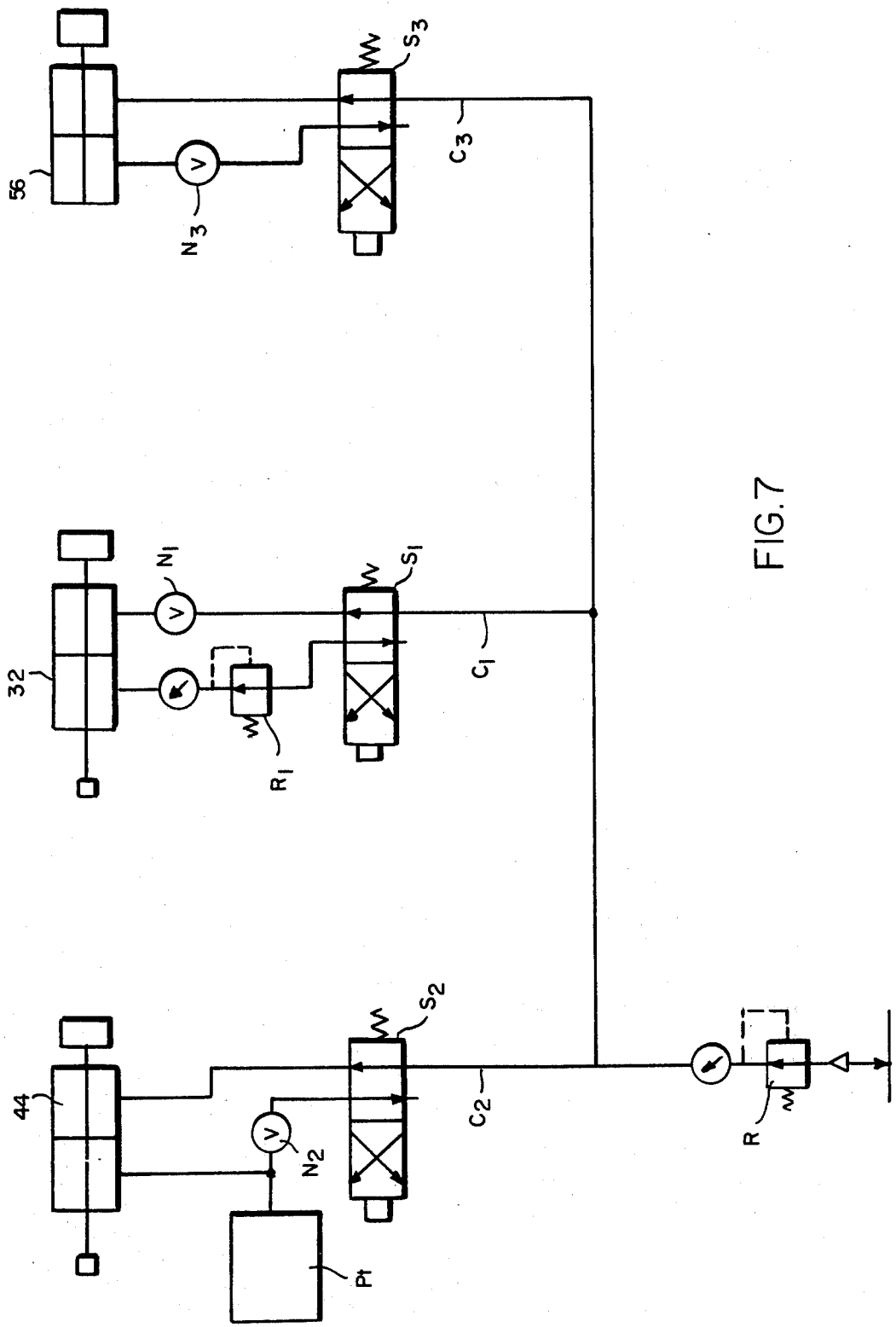

FIG. 7 diagrammatically illustrates the pneumatic system; and

Figure 8:
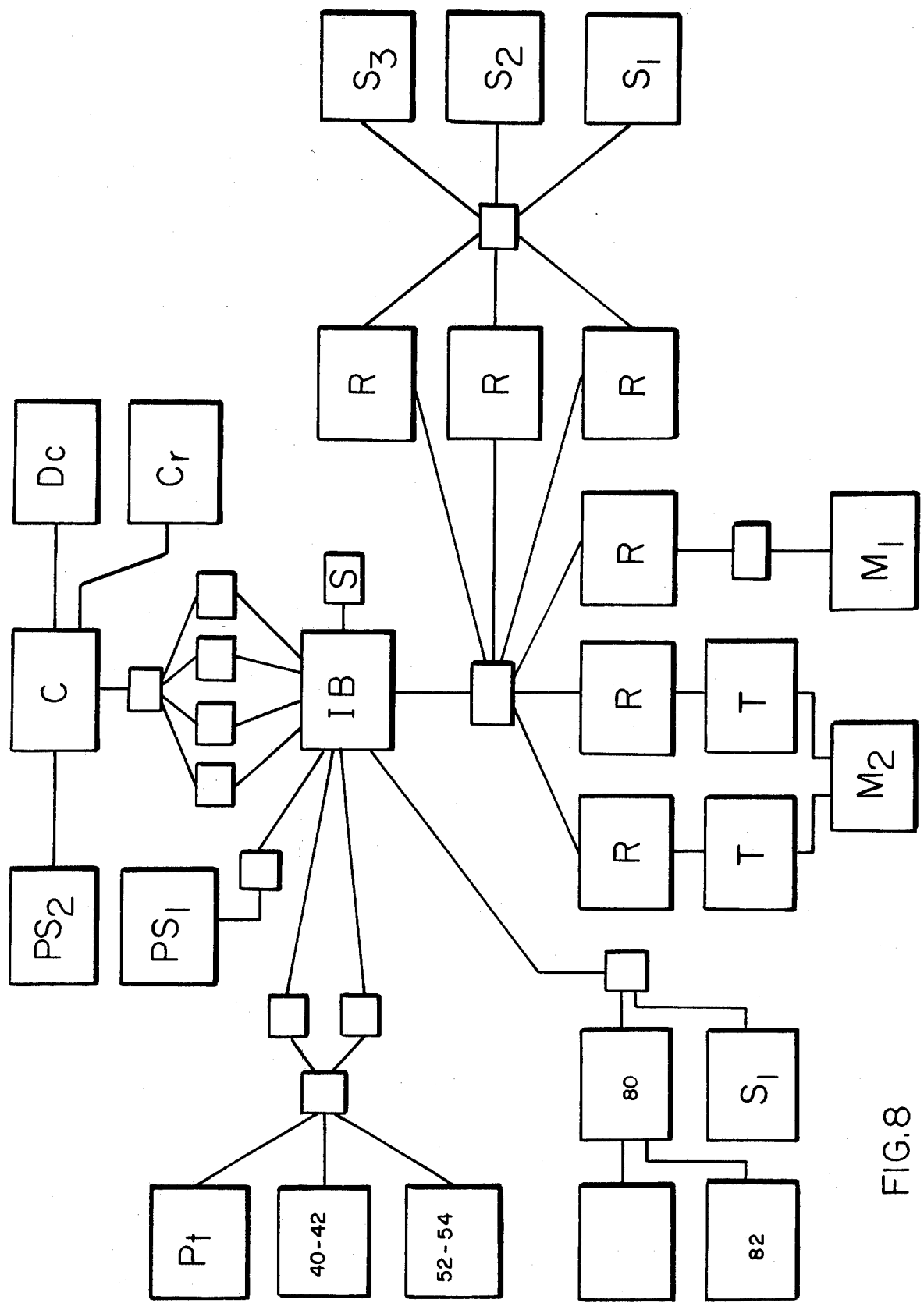

FIG. 8 diagrammatically illustrates the control system.

Figure 1:
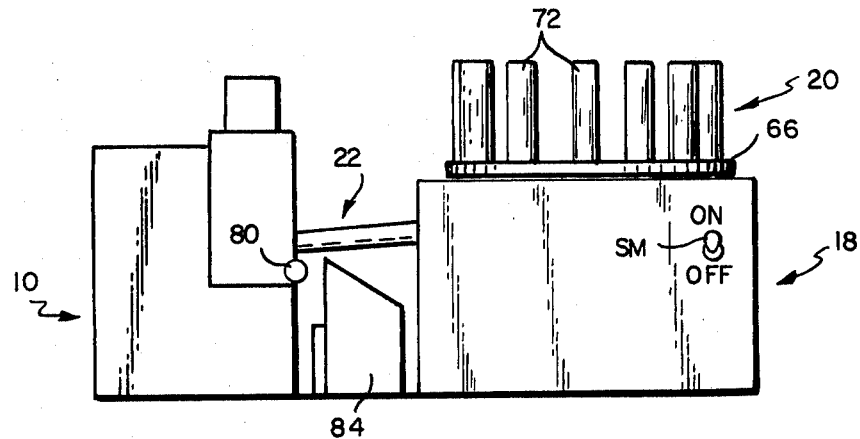
FIG. 1 is an elevation of the apparatus.
Figure 2:
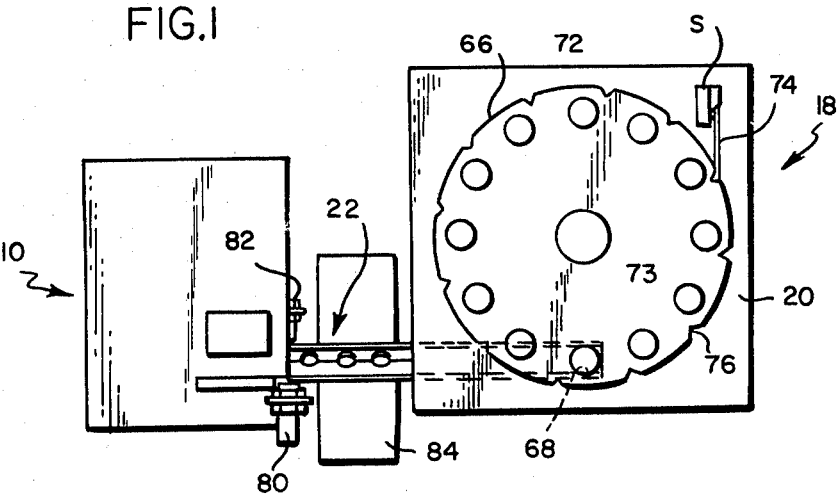
FIG. 2 is a plan view of the apparatus.
Figure 3:
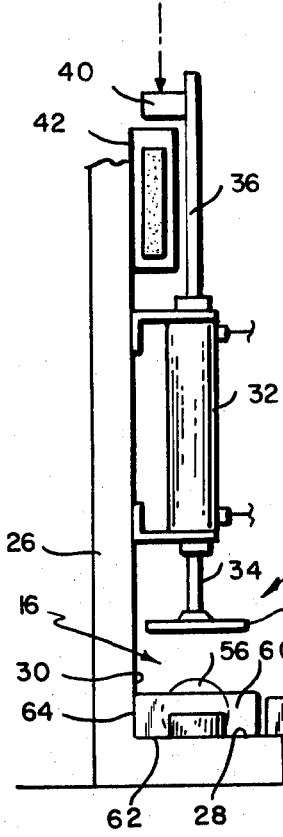
FIG. 3 is a diagrammatic elevation to much larger scale showing the gauge for measuring thickness, the ram for measuring diameter and hardness and the scraper for scraping the supporting surface clear of broken tablets.
Figure 4:
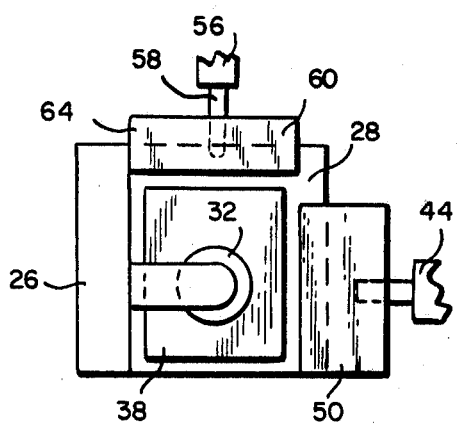
FIG. 4 is a plan view taken on the line 4—4 of FIG. 3.

Referring to the drawings, FIGS. 1, 2 and 3, there is shown a structure 10 providing a support for a tablet to be tested, a gauge 12 for measuring the thickness of a tablet resting on the support, a ram 14 for measuring the diameter of the tablet and its breaking strength, and a scraper 16 for removing the broken tablet from the support, the structure including means for effecting reciprocation of the several components comprising the gauge for measuring the thickness, the ram for measuring the diameter and breaking strength, and the scraper for removing the broken tablets and a second structure 18 upon which there is mounted a carousel 20 for supplying groups of tablets of a predetermined number of tablets to the support for testing, including an inclined trough 22 for transferring the tablets from the carousel to the support and control circuitry.

Figure 6:
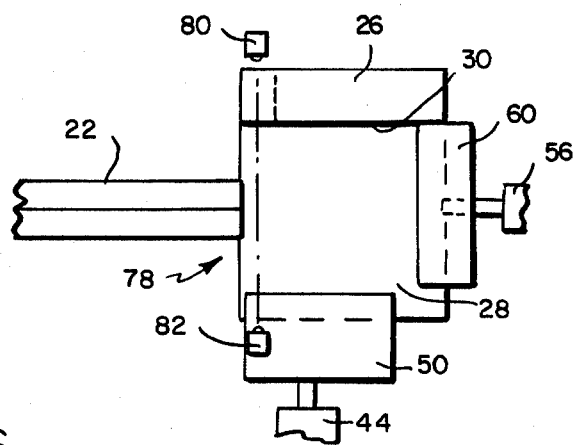
FIG. 6 is a plan view taken on the line 6—6 of FIG. 5.

More specifically, the structure 10 includes a support 26 having a stationary, unyielding, flat, horizontal surface 28 and a stationary, unyielding, flat, vertical surface 30, the surface 28 as shown in FIG. 6 being of substantially rectangular configuration. The structure 10 provides support for a vertically-disposed cylinder 32 within which there is reciprocally mounted a piston provided with piston rods 34 and 36 extending, respectively, from the lower end of the cylinder 32 and the upper end of the cylinder 32. The gauge 12 comprises a flat gauge plate 38 fixed to the lower extremity of the rod 34 and a diode 40 attached to the extremity of the upwardly-extending rod 36. The cylinder 32 is double-acting in that air supplied to one end forces the piston therein downwardly and at the other end forces the piston therein upwardly so as to enable reciprocating the gauge plate 38 perpendicularly with respect to the horizontal surface 28 of the support 26. A photopotentiometer 42 is mounted to the support 26 adjacent the upwardly-extending rod 36 so that the diode 40 traverses its surface and according to the position that is occupied with reference to the surface measures the thickness of a tablet resting on the surface 28. The structure 10 also provides support for a horizontally-disposed cylinder 44 containing a piston from which project at opposite ends rods 46 and 48. The ram 14 comprises a block 50 secured to the rod 46 and movable parallel to the surface 28 and at right angles to the surface 30. The cylinder 44 is double-acting so that pressure applied to one end moves the ram toward the surface 30 and the other end retracts the ram and there is a diode 52 attached to the rod 48 which is movable with the piston in reciprocation relative to a photopotentiometer 54 to measure the diameter of a tablet resting on the surface 28.

The structure 10 additionally provides support for the scraper 16 which comprises a cylinder 56 provided with a piston from one end of which projects a piston rod 58 to the extremity of which is secured a block 60 having a flat surface 62 parallel to the surface 28 and a flat surface 64 at right angles to the surface 62 and parallel to the surface 30 movable across the surfaces 28 and 30 and relative to the surfaces 28 and 30 to clear these surfaces of any particles of broken tablets which are broken by the ram when the latter is moved to the extent of breaking the tablet. The cylinder 56 is double-acting so that air applied to one end retracts the scraper and to the other end advances the scraper.

The carousel 20 comprises a flat, horizontally-disposed plate 66 fixed to a vertically-positioned shaft 73 driven by a motor, not shown, supported below the top 66 within the structure 18. The carousel has mounted peripherally thereof a plurality of cylindrical containers 72 which are open at the top and bottom. These containers 72 are dimensioned to receive a predetermined number of tablets and to release the tablets therefrom as they are moved into alignment with a hole 68 in the top of the structure 18. The carousel is rotated to position the containers successively above the opening 68 for testing of a group of tablets by means of the aforesaid motor, the operation of which is controlled by a switch S provided with a switch arm 74 which bears against the edge of the carousel and is actuated to disable the switch by notches 76 at the edge of the carousel.

Figure 5:
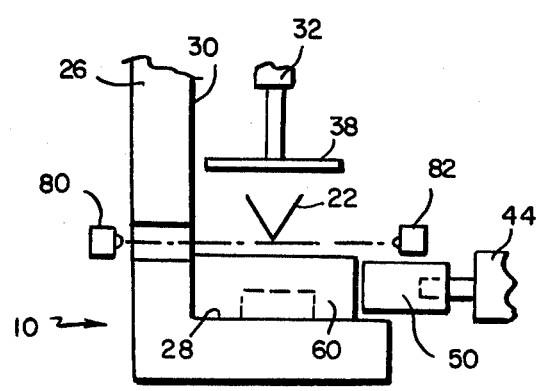
FIG. 5 is a fragmentary elevation looking at the lower end of the inclined trough.

The tablets which are released from the containers 72 gravitationally drop through the hole 68 onto the upper end of the trough 22 which is, as shown in FIG. 5, of V-shaped cross section. The upper end of the trough is supported within the structure 18 below the opening 68 and the lower end is supported directly above the supporting surface 28 so that tablets sliding down the inclined trough are deposited on the surface 28. A conventional vibrator within the structure, not shown, provides for effecting vibration of the trough 22 so that the tablets deposited on its upper end are caused to slide down the trough and to drop one at a time onto the surface 28. In order to determine when a tablet has dropped onto the surface 28 and to initiate a cycle of operation, that is, to wit, a cycle which involves measuring the thickness, the diameter, crushing the tablet to determine hardness and sweeping the crushed parts from the surface, there is provided a photosensing device 78 comprising, as shown in FIGS. 5 and 6, a light-sensitive cell 80 and a light source 82 positioned on the structure 10 adjacent the lower end of the trough so that when a tablet drops from the lower end of the trough onto the surface 28, it will pass through the beam from the light source to the cell and by interruption of the beam, produce a signal which disables the vibrator so that only a single tablet will drop from the trough onto the testing surface. Ideally, the vibration can be controlled so that the tablet slides down the trough in such spaced relation that only one tablet at a time drops onto the testing surface and the vibration is stopped before the next tablet is precipitated from the end of the trough. Sometimes, however, a second tablet will drop onto the testing surface and, as will be described hereinafter, the control circuit is so conditioned that if a second signal is received from the photosensing device within a predetermined interval after the first, the vibrator will be disabled and the scraper will be caused to move across the surface of the support 28 to clear the surface of the two tablets and the vibrator will be reenabled to cause another tablet to be deposited on the testing surface.

A can 84 is positioned between the structures 10 and 18 adjacent the lower end of the trough to receive the whole or crushed tablet cleared from the supporting surface by the scraper.

The pneumatic system by means of which air pressure is supplied to the cylinder piston assemblies which effects reciprocation of the gauge 12, ram 14 and sweeper scraper are shown in FIG. 7, together with four-way, direct-acting solenoid valves and their connection to a source of air pressure. Referring to FIG. 7, air is supplied at a pressure of approximately 70 pounds per square inch from a suitable source through an air regulator R and conductors C1, C2 and C3, respectively, to the double-acting cylinders 32, 44 and 46. In each of the conductors, there is a four-way, direct-acting solenoid valve, respectively, S1, S2 and S3. Between the four-way solenoid valve S1 and the cylinder 32, there is a needle valve N1 and an air regulator R1, the latter being set for a relatively low pressure of 5 pounds per square inch so as to cause the gauge plate 38 to engage the tablet at a very low pressure. Between the solenoid-actuated valve S2 and the cylinder 44, there is a needle valve N2 and a pressure transducer PT, the purpose of which is to produce a signal when the pressure drops in the cylinder 44 as the result of sudden crumbling of the tablet indicative of the crushing pressure. There is a needle valve N3 between the solenoid-actuated valve S3 and the cylinder 56.

The control circuitry as shown in FIG. 8 is illustrated by way of a block diagram and referring thereto, there is shown a power supply PS, which supplies power to an interface board IB to which are connected the pressure transducer PT, the photopotentiometer 42 and diode 40, the photopotentiometer 54 and diode 52, the photosensor comprising the diode 82 and transistor 80, the carousel switch S, the four-way solenoid valves S1, S2 and S3, the carousel motor M1, and the vibrator motor M2, together with appropriate relays R and variable transformers T. The interface board IB is, in turn, connected to a computer C comprising a Dynabyte basic controller supplied with power from a power supply PS2 to which are connected a terminal printer DC and a cassette recorder CR.

The computer is conditioned to cycle the apparatus described above in such a way as to test each one of the tablets in the successive groups of tablets which are presented for testing by the carousel to average the dimensions, the range of dimensions and out of line dimensions. With the pressure supply suitably connected to a source of pressure and the power supply to a source of power, a cycle of operation which, as previously mentioned, comprises testing all of the tablets contained in a single container resting on the carousel is initiated by the computer C by the operator typing the appropriate command. The computer C starts the carousel motor M1, whereupon the carousel rotates until the switch arm 74 of the switch S falls into a notch 76 so as to stop the carousel motor M2. At the stopped position, the tablets in a container 72 gravitate through the hole 68 onto the upper end of the trough 22, vibration of which is initiated by the computer. The tablets are caused by such vibration to proceed down the inclined trough and when the first tablet drops off, it passes through the light beam between the diode 82 and the phototransistor 80. The signal produced by interruption of the beam deactivates the vibrator motor M2 and if within a predetermined interval a second tablet does not drop onto the support, a signal is generated which causes the four-way valve S1 to be actuated to supply pressure to the cylinder 32 to move the gauge plate 38 downwardly into engagement with a tablet resting on the support and by way of the diode 40 and photopotentiometer 42 to measure the thickness of the tablet, produce an appropriate signal and then effect retraction of the gauge plate. This is followed by actuation of the four-way valve S2 which moves the ram 50 across the support to first engage the diametral dimension of the tablet to provide a signal by way of the diode 52 and photopotentiometer 54 appropriate to the dimension and for further movement to cause crushing of the tablet, whereupon the pressure transducer PT provides a signal appropriate to the crushing pressure followed by retraction of the ram. Following this, pressure is supplied to the four-way valve S3 to advance the scraper 56 across the surface to sweep the broken particles of the tablet off the surface into the can 84 and then to retract the scraper. This completes the cycle. The control circuitry is programmed to repeat the cycles until all or so many as may be desired of the containers are emptied.

It should be understood that the present disclosure is for the purpose of illustration only and includes all modifications or improvements which fall within the scope of the appended claims.

We claim:

1. Apparatus for testing medicinal tablets for thickness, diameter and hardness comprising a support for receiving tablets one at a time for testing, means movable relative to the support in a direction perpendicular to the thickness of the tablet to measure the thickness of the tablet, means movable relative to the support in a direction at right angles to the thickness of the tablet to measure the diameter of the tablet, said latter means being further movable to crush the tablet to thus measure the hardness, and means for effecting reciprocal movement of the aforesaid means in sequence and for repeating said sequence of operation for a predetermined number of tablets.

2. Apparatus according to claim 1 wherein the support comprises a flat, unyielding, horizontal, smooth surface and a flat, unyielding, smooth vertical surface and wherein the first means is movable perpendicularly with respect to the horizontal surface and the second means is movable perpendicularly with respect to the vertical surface.

3. Apparatus according to claim 1 wherein the first and second means are, respectively, a thickness gauge and a ram, the third means comprises power-operable devices for effecting reciprocation of the first and second means to, respectively, advance the gauge into engagement with the tablet to measure its thickness and then retract from it, advance the ram into engagement with the tablet to measure the diameter, crush it and then retract from it and means movable relative to the horizontal surface following retraction of the ram to sweep the crushed tablet from the support.

4. Apparatus according to claim 3 wherein the last-named means is a scraper provided with right-angularly disposed surfaces which, respectively, have scraping contact with the horizontal and vertical surfaces of the support.

5. Apparatus according to claim 4 wherein said scraper is reciprocal and there is means for effecting its reciprocation in the sequence of operation.

6. Apparatus according to claim 3 wherein the means for effecting reciprocation of the gauge and ram comprise double-acting cylinder and piston assemblies.

7. Apparatus according to claim 6 wherein the piston rods extend from the pistons through the opposite ends of the cylinders, the gauge and ram are fixed to the extremities of the rods at one end and there is means fixed to the extremities of the rods at the other ends for determining the measurements.

8. Apparatus according to claim 7 wherein the piston rods extend from the pistons through the opposite ends of the cylinders, the gauge and ram are fixed to the extremities of the rods at one end and there are sensing means at the other ends of the rods for determining the measurements.

9. Apparatus according to claim 8 wherein the means at the other ends comprise diodes mounted to the rods for movement therewith and stationarily supported photopotentiometers supported to be traversed by the diodes.

10. Apparatus according to claim 7 wherein there is a pressure transducer connected to the cylinder containing the ram operable by the change in pressure when the tablet fails to register the breaking pressure.

11. Apparatus for testing medicinal tablets for thickness, diameter and hardness comprising a support for receiving tablets one at a time, a gauge supported for reciprocal movement perpendicular to the support to measure the thickness, a ram supported for reciprocal movement relative to the support at right angles to the reciprocal movement of the gauge to measure the diameter and hardness and means for delivering tablets from a predetermined group of tablets onto the support one at a time comprising an inclined trough supported with its lower end above the support, means for delivering tablets to the upper end of the inclined trough and means for vibrating the trough.

12. Apparatus according to claim 11 wherein the means for delivering tablets to the upper end of the trough comprising a part containing a hole of such size as to permit tablets to pass through positioned above the upper end of trough and means for supplying a quantity of tablets from a predetermined number through the hole.

13. Apparatus according to claim 11 wherein the means for delivering tablets to the upper end of the trough comprise a stationary part containing a hole of such size as to permit tablets to pass through, a rotary carousel provided with a plurality of tubular containers spaced peripherally thereof open at their top and bottom ends with their lower ends adjacent the stationary part, rotatable relative to the part to position the lower open ends of the containers successively above the hole, means for effecting rotation of the carousel and means for controlling operation of the last-named means to stop each container in succession above the hole in the part.

14. Apparatus for testing tablets comprising a stationary structure defining a smooth, flat, unyielding surface, a mobile structure defining a smooth, flat, unyielding surface, movable relative to the stationary surface to gauge a tablet deposited between the surfaces of the structures, one of said structures embodying sensing means operable at the gauging position to measure a physical property of a tablet deposited between said surfaces and means responsive to the sensing means to store the measurement of each individual tablet of a predetermined group of tablets, average the measurements, record the range of measurements, and record the out of line measurements, a dispenser for receiving a predetermined number of tablets, an inclined chute for guiding tablets gravitationally received from the dispenser for deposit at gauging position, and means for vibrating the chute to cause the tablets to be deposited one at a time, means operative in response to the presence of more than one tablet at gauging position to disable the vibrating means, clear the tablets from gauging position and then enable the vibrating means.

15. Apparatus for testing tablets comprising a stationary platen having a flat planar surface, means for depositing tablets to be measured one at a time on the surface, means defining a stationary surface perpendicular of the surface of the platen and means supported above the platen for movement parallel to the platen relative to the stationary surface, said last mentioned means being determinative of the diameter of the tablet resting on the surface and embodying means for effecting recording of the diameter of the tablet, said means supported for movement parallel to the platen enables means determinative of the force required to crush the tablet.

16. Apparatus according to claim 15 wherein said last-named means comprises a pressure transducer.

* * * * *